United States Patent [19]
Bossen et al.

[11] Patent Number: 5,276,327
[45] Date of Patent: * Jan. 4, 1994

[54] SENSOR AND METHOD FOR MESAUREMENT OF SELECT COMPONENTS OF A MATERIAL

[75] Inventors: David A. Bossen, Palo Alto; Lee M. Chase, Los Gatos; Leonard M. Anderson, San Jose; Michael K. Norton, Los Gatos, all of Calif.

[73] Assignee: Measurex Corporation, Cupertino, Calif.

[*] Notice: The portion of the term of this patent subsequent to May 4, 2010 has been disclaimed.

[21] Appl. No.: 803,967

[22] Filed: Dec. 9, 1991

[51] Int. Cl.$^5$ .................... G01N 21/35; G01N 21/25; G01N 33/34
[52] U.S. Cl. .................... 250/339; 250/341
[58] Field of Search .............. 250/341, 339; 356/238

[56] References Cited

U.S. PATENT DOCUMENTS

| | | | |
|---|---|---|---|
| 3,228,282 | 1/1966 | Barker, Jr. | 356/429 |
| 3,405,268 | 10/1968 | Brunton | 250/339 |
| 3,455,637 | 7/1969 | Howard | 356/434 |
| 3,476,482 | 11/1969 | Howard et al. | 356/446 |
| 3,525,863 | 8/1970 | Constantine et al. | 378/45 |
| 3,614,450 | 10/1971 | Hill et al. | 250/205 |
| 3,641,349 | 2/1972 | Dahlin | 250/350 |
| 3,675,019 | 7/1972 | Hill et al. | 250/350 |
| 3,793,524 | 2/1974 | Howarth | 250/339 |
| 3,801,349 | 4/1974 | Wilson et al. | 427/10 |
| 3,827,808 | 8/1974 | Cho | 356/429 |
| 3,851,175 | 11/1974 | Dahlin et al. | 250/339 |
| 3,879,607 | 4/1975 | Bjorklund | 250/252.1 |
| 3,965,356 | 6/1976 | Howarth | 250/343 |
| 3,994,602 | 11/1976 | Howarth | 356/442 |
| 4,006,358 | 2/1977 | Howarth | 250/339 |
| 4,098,641 | 7/1978 | Casey et al. | 162/198 |
| 4,135,006 | 1/1979 | Readel et al. | 427/10 |
| 4,243,882 | 1/1981 | Yasujima et al. | 250/339 |
| 4,277,177 | 7/1981 | Larsen et al. | 356/431 |
| 4,306,151 | 12/1981 | Chase | 250/341 |
| 4,319,847 | 3/1982 | Howarth | 356/341 |

(List continued on next page.)

FOREIGN PATENT DOCUMENTS

| | | |
|---|---|---|
| 0137696 | 4/1985 | European Pat. Off. |
| 2128273 | 6/1971 | Fed. Rep. of Germany |
| 2318032 | 10/1973 | Fed. Rep. of Germany |
| 2845995 | 4/1979 | Fed. Rep. of Germany |
| 53-39194 | 10/1978 | Japan |
| 59-120940 | 7/1984 | Japan |
| 61-53549 | 3/1986 | Japan |

(List continued on next page.)

OTHER PUBLICATIONS

Jon F. Pugh, "The infrared measurement of surface moisture in paper." Tappi, vol. 63, No. 10 (Oct. 1980) pp. 131-134.

Wesley Wm. Wendlandt and Harry G. Hecht, *Reflectance Spectroscopy* New York, Interscience Publishers, 1966, pp. 46-90.

K. Takami and G. Shinbo, *Thickness measurement method for thin photoresist film on transparent material*, Rev. Sci. Instrum. 54(6), Jun. 1983.

*Primary Examiner*—Constantine Hannaher
*Attorney, Agent, or Firm*—Spensley, Horn, Jubas & Lubitz

[57] ABSTRACT

A sensor and method is provided for measuring one or more select components of a material. In one embodiment, a method measures the components by emitting electromagnetic radiation at the material and detecting the intensity of the emerging radiation at separate locations from the source. In another embodiment, a sensor provides a radiation source for emitting radiation at a sheet, a plurality of detecting means, offset substantially the same from the source, for detecting radiation after interaction with the sheet and first and second reflectors for directing the radiation so that the radiation makes multiple interactions with the sheet when moving from the source to the detecting means. The invention can accurately measure the select components (e.g., moisture) of different grades of paper by eliminating the effects of the scattering power and determining absorption power at each band of the spectrum considered necessary for a particular measurement.

25 Claims, 7 Drawing Sheets

U.S. PATENT DOCUMENTS

| | | | |
|---|---|---|---|
| 4,345,150 | 8/1982 | Tamura et al. | 250/339 |
| 4,743,775 | 5/1988 | Edgar | 250/571 |
| 4,769,544 | 9/1988 | Dahlquist | 250/339 |
| 4,789,820 | 12/1988 | Parrent, Jr. et al. | 324/640 |
| 4,823,008 | 4/1989 | Sturm | 250/339 |
| 4,840,706 | 6/1989 | Campbell | 162/198 |
| 4,928,013 | 5/1990 | Howarth et al. | 250/339 |
| 4,957,770 | 9/1990 | Howarth | 427/9 |
| 5,124,552 | 6/1992 | Anderson | 250/339 |

FOREIGN PATENT DOCUMENTS

| | | |
|---|---|---|
| 61-120004 | 6/1986 | Japan . |
| 1102062 | 2/1968 | United Kingdom . |
| 2044443 | 10/1980 | United Kingdom . |
| 2127871 | 4/1984 | United Kingdom . |

SENSOR AND METHOD FOR MESAUREMENT OF SELECT COMPONENTS OF A MATERIAL

BACKGROUND OF THE INVENTION

(1) Field of the Invention

The invention relates to the field of sensors and methods for measuring one or more select components of a material. In particular, the invention relates to measuring the components by emitting electromagnetic radiation at the material and detecting the amount of emerging radiation at separate locations. The invention can accurately measure the components (e.g., moisture) of different grades of paper by eliminating the effects of the scattering power and determining absorption power at each band of the spectrum necessary for the particular measurement.

(2) Description of the Related Art

Because paper is produced in a sheet from an aqueous suspension, which includes wood pulp fibers, cotton fibers and various chemicals, it initially contains a considerable amount of moisture. Most of this moisture is removed during paper production. However, for a variety of reasons, it is often desirable to include at least some moisture in the paper. For example, if the paper is too dry, it will tend to curl at the edges or may increase the cost of production.

A paper sheet is typically dried by passing it around heated drying drums. However, this tends to dry the sheet unevenly across its cross-direction width, producing paper of uneven quality. Devices have been developed to selectively moisten or dry the cross-directional sections of the sheet. U.S. Pat. No. 5,020,469 to Boissevain et al., assigned to Measurex Corporation, describes such a device. Typically, the moistening or drying occurs after the sheet has passed around the drying drums. Of course, the paper mill operator, or the paper mill's process control computer, must determine the cross-directional moisture profile of the sheet before these devices can be used effectively. Thus, moisture sensors have been developed to measure the cross-directional moisture profile.

Water absorbs electromagnetic radiation across the infrared spectrum as a function of wavelength. Some moisture sensors take advantage of this phenomenon by emitting infrared radiation at the sheet and detecting the amount of the radiation passing through or reflected from the sheet at or near the water absorption peak. The more moisture in the sheet, the less radiation at or near the water absorption peak that will pass through or be reflected from the sheet.

An infrared moisture sensor can be set up with an infrared radiation source located on one side of the sheet and two detectors on the opposite side. Each detector has an associated band pass filter positioned between the source and the detector so that the detector only receives radiation in a select band of the spectrum. A first band pass filter passes that portion of radiation which is near a water absorption peak to a first detector. Thus, the first detector is primarily sensitive to the amount of water in the sheet and receives more infrared radiation when the sheet is dry and less infrared radiation when the sheet is moist.

A second band pass filter passes radiation in a band of the spectrum where there is less moisture absorption. In this band, most of the absorption is from sheet fibers rather than moisture in the sheet. Thus, when the basis weight (i.e., weight per unit area) of the sheet fiber increases, the second detector receives less infrared radiation. The output of the second detector corrects for changes in the basis weight of the sheet fiber. When the outputs from these two detectors are properly combined, the sensor provides an accurate measurement of the moisture in the sheet so that the changes in the basis weight of the sheet fiber do not affect the moisture measurement.

U.S. Pat. No. 4,928,013 to Howarth et al., assigned to Measurex Corporation, describes an infrared moisture sensor of this type with two band pass filters that are selected to compensate for sheet temperature changes which shift the absorption spectrum to either shorter or longer wavelengths. In this sensor, a first band pass filter, associated with a measure detector, is selected so that it is surrounds the water absorption peak at about 1.93 microns. When the sheet temperature increases, the intensity of radiation increases at the long wavelength side of the pass band filter while an approximately equal decrease occurs at the short wavelength side. Accordingly, the amount of infrared radiation reaching the measure detector remains substantially constant when the sheet temperature changes. A second band pass filter, associated with a reference detector, is selected so that it is in a band of the infrared spectrum that is predominantly absorbed by the sheet fibers. The intensity of the radiation detected by the reference detector primarily indicates the basis weight of the sheet.

However, the intensity of the detected radiation is not only dependent upon the moisture, basis weight and temperature of the sheet. Each grade of sheet has its scattering and absorption powers that affect the intensity of the detected radiation. A scattering power of a material defines its ability to change the direction of light incident upon the material from either the line of incidence when transmitted through or from a specular direction when reflected from the material. An absorption power defines the material's ability to absorb the incident light rather than allow it to be transmitted through or reflected from the sheet.

The source of the wood fiber used to make paper products may affect the value of the scattering coefficient and/or the broadband absorption coefficients. This in turn may affect the accuracy of an infrared moisture sensor. Changes in the scattering power of paper are often caused when the source of the paper pulp changes from one species of wood to another or from virgin to recycled fiber. Broadband absorption change may be caused by the carbon black in printer inks used in recycled paper or added to colored paper.

U.S. Pat. No. 3,793,524 to Howarth, assigned to Measurex Corporation, describes an infrared moisture sensor for measuring the moisture of a sheet of material such as paper. The moisture sensor includes an infrared source that directs infrared radiation out of an aperture through paper and into another aperture to a detector. The source and detector apertures are located in opposing reflective paper guides disposed on either side of the paper and are offset from one another so that the radiation is reflected repeatedly back and forth between the paper guides in traveling from the source aperture and to the detector aperture (FIG. 2). The offset geometry results in relatively low sensitivity to the scattering power of the paper but may require calibration to measure different grades of paper. It would be highly desirable to have a moisture sensor which has one calibration for a broad range of grades of paper. To achieve this goal any sensitivity to the scattering power must be eliminated.

SUMMARY OF THE INVENTION

The present invention relates to a sensor and method for measuring one or more select components (e.g., moisture) of a material by emitting radiation at the material and detecting the amount of radiation emerging from the material at separate locations from the radiation source after the radiation has multiple interactions with the material.

In one embodiment, the invention provides a sensor for measuring select components of a material such as a sheet, including: (1) a radiation source for emitting radiation at a sheet; (2) a plurality of detecting means, with substantially the same offset from the source, for detecting radiation after interaction with the sheet; and (3) means for directing the radiation so that the radiation makes multiple interactions with the sheet when moving from the source to the detecting means.

In another embodiment, the invention provides a sensor for measuring select components such as the moisture of a sheet, including: (1) a source for emitting radiation through a source aperture; (2) means for detecting radiation after multiple interactions with the sheet, including at least two apertures, with the substantially the same offset from the source aperture, for receiving the radiation; and (3) first and second reflector means for directing the radiation so that the radiation has multiple interactions with the sheet when moving from the source to the detecting means.

BRIEF DESCRIPTION OF THE DRAWINGS

The objects, features and advantages of the invention will become more apparent from the following detailed description of the preferred embodiments taken in conjunction with accompanying drawings, in which.

DETAILED DESCRIPTION OF THE PREFERRED EMBODIMENTS

The following description covers the best mode of carrying out the invention. For the sake of simplicity the invention will be described primarily as measuring the amount of moisture in a paper sheet by use of infrared radiation. However, this is only to illustrate the principles of the invention and should not be taken in a limiting sense. The principles of the invention may be also used to measure other select components or physical properties (e.g., basis weight) of a sheet of other types of materials (e.g., plastic film) with other forms of electromagnetic radiation (e.g., ultraviolet and visible light). Therefore, the scope of the invention is best determined by reference to the appended claims. In the accompanying drawings like numerals designate like parts.

Figure 1:
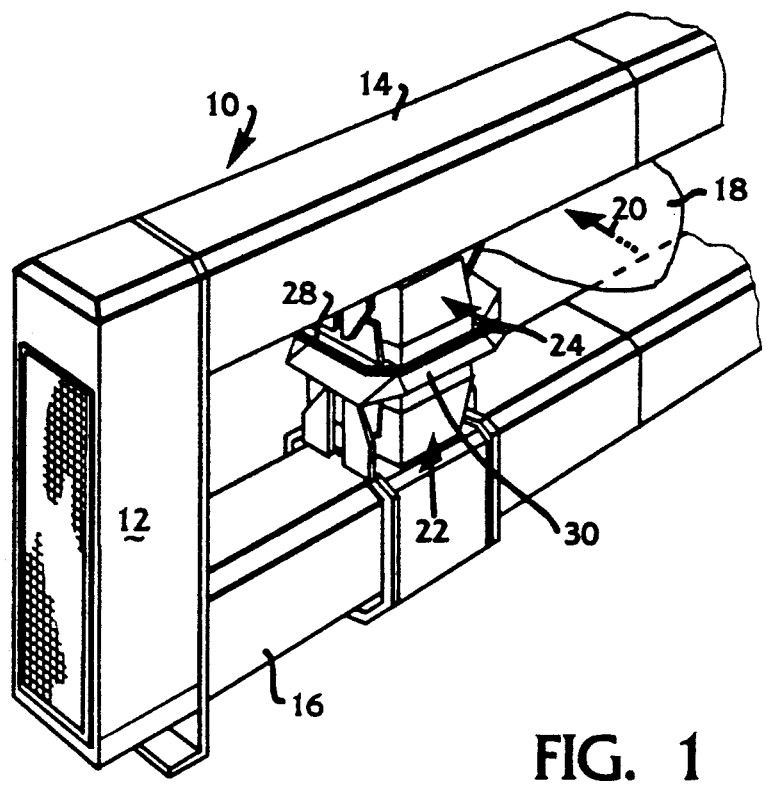
FIG. 1 is a partial perspective view of a sensor mounted on a scanner which moves back and forth in the cross-direction across the sheet.

FIG. 1 illustrates a scanner 10 which includes a framework 12 of a pair of spaced upper and lower parallel beams 14 and 16 extending in the cross-direction across the sheet of material or paper 18. Paper 18 travels through the scanner 10 in the direction shown by arrow 20. Lower and upper gauging heads 22 and 24 are provided on the framework 12 and travel longitudinally of framework 12 and in the cross-direction of paper 18.

Figure 2:
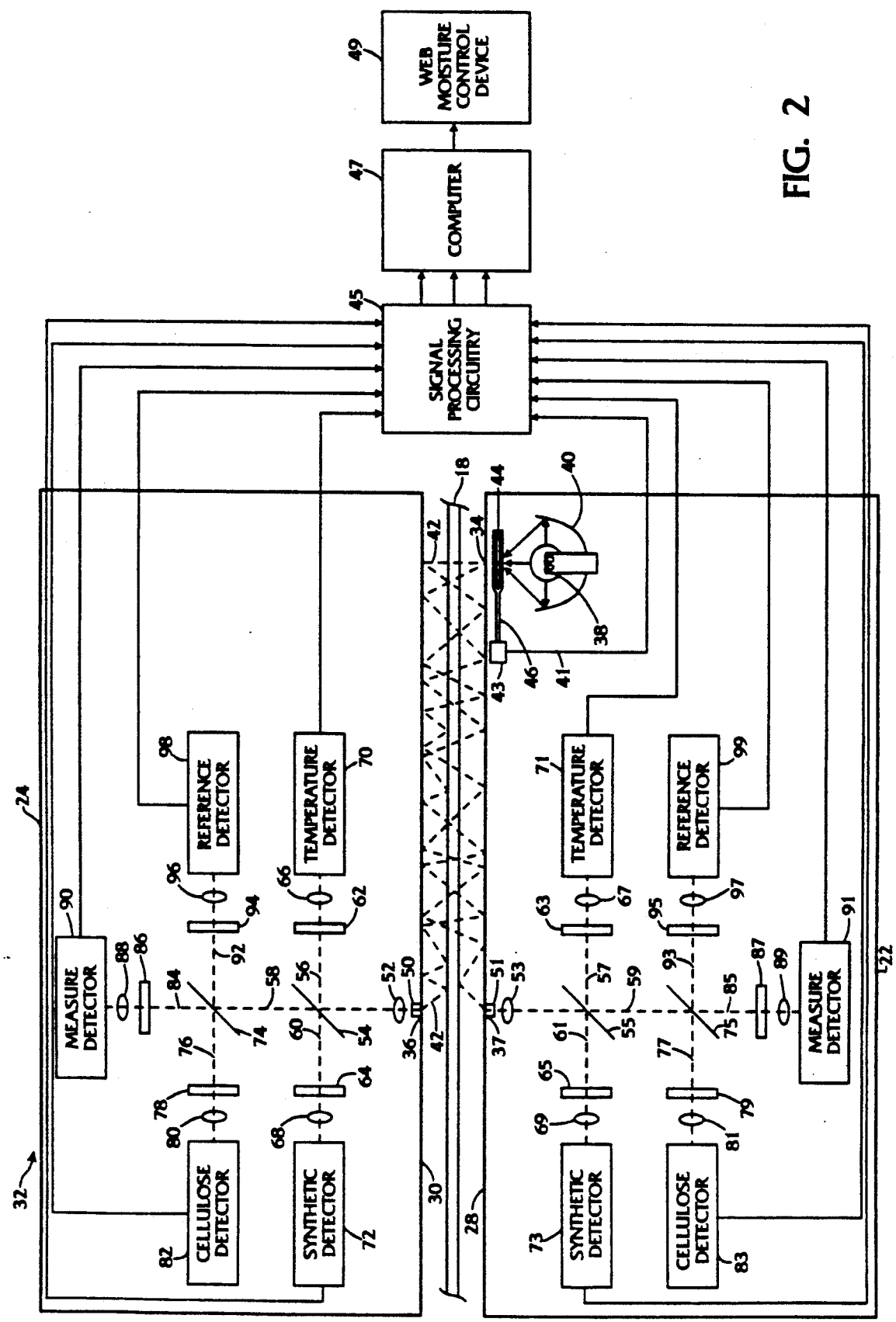
FIG. 2 is a schematic elevation view illustrating an embodiment of a sensor according to the present invention.

FIG. 2 illustrates an infrared moisture sensor 32. It includes a lower head 22 with a radiation source for directing infrared radiation 42 through a source aperture 34 to paper 18. Favorable results were achieved by using a radiation source including an incandescent lamp 38 and an elliptical reflector 40 with a source aperture 34 of about ⅛ inch in diameter. It is preferred, but not necessary to the invention, that the amount of radiation emitted from lamp 38 and falling on paper 18 be modulated at a known frequency.

This modulation may be accomplished by any one of several devices. For example, the tines 44 of a tuning fork 46 may be disposed in the path of the radiation 42. The vibrating tines 44 modulate the radiation 42 as the tines 44 move alternatively in and out of the path of radiation 42. Alternatively, an opaque disk (not shown) having a plurality of evenly spaced radial slots may be rotated in the path of the radiation so that the radiation is alternately transmitted through the slots and blocked by the opaque portions of the disk. With either device, radiation 42 is modulated at a known frequency The reason for modulating the radiation is explained below.

Figure 3A:
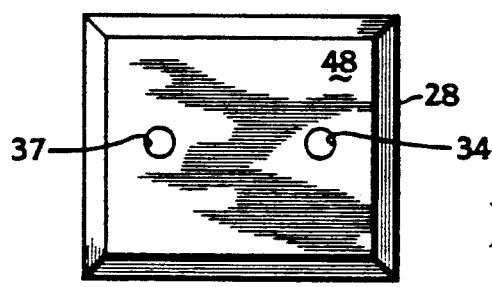
FIG. 3a illustrates a reflective paper guide of the lower head of the sensor with a source and detector aperture.
Figure 3B:
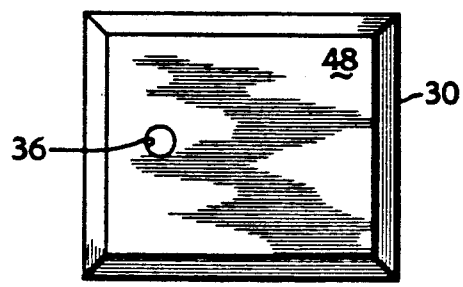
FIG. 3b illustrates a reflective paper guide of the upper head of the sensor with a detector aperture.

The lower and upper heads 22 and 24 include opposing surfaces which function as paper guides 28 and 30. Each of the guides 28 and 30 includes a reflective coating 48 (FIGS. 3a and 3b) for directing radiation from source aperture 34 to detector apertures 36 and 37. FIG. 3a illustrates that guide 28 includes a reflective coating 48, a source aperture 34 and a detector aperture 37. FIG. 3b illustrates that guide 30 has a similar reflective coating 48 and a detector aperture 36. Reflective coating 48 is preferably a non-specular or diffuse reflective surface. For example, coating 48 may consist of a layer of translucent quartz or glass ceramic backed by a reflective material. To provide an easily cleaned surface the surfaces of guides 28 and 30 may be anodized aluminum. In one preferred embodiment, the guides 28 and 30 may consist of two diffuse reflective parallel plates about 0.4 inches apart.

In the embodiment of FIG. 2, radiation 42 is reflected back and forth between lower and upper guides 28, 30, before entering detector apertures 36 and 37. This ensures that radiation 42 makes multiple interactions with paper 18, that is, passes through the paper 18 a number of times. This provides certain advantages when measuring the moisture content of very light grades of paper, such as tissue, and very heavy paper grades. This technique and the advantages of such multiple interactions with the paper sheet are more fully discussed in U.S. Pat. No. 3,793,524 to Howarth, assigned to Measurex Corporation, which is incorporated herein by reference.

Radiation 42 from source aperture 34 reaches detector apertures 36 and 37 by a somewhat complex set of paths, partially illustrated by the dashed lines. The radiation 42 initially impinges on paper 18 with part of the radiation 42 passing through and part being reflected by the paper 18. Guides 28 and 30 reflect this radiation 42 back to the paper 18 where it undergoes the same process of partial transmission and reflection. In addition, the paper 18 itself, being translucent, acts to diffuse the radiation 42 to increase the number of paths.

The mean number of times the radiation 42 passes through the paper 18 on its path from the source aperture 34 to the detector apertures 36 and 37 can be easily controlled by adjusting the geometry of sensor 32. In this manner, paper 18 can be made to appear thicker than its actual thickness.

The radiation 42 enters upper head 24 through detector aperture 36. The upper head 24 includes a light pipe 50 which guides the radiation 42 to a lens 52 which collimates the radiation. The first beam splitter 54 splits the radiation 42 into three separate beams 56, 58 and 60. Band pass filters 62 and 64 are positioned in the respective paths of beams 56 and 60. Lenses 66 and 68 focus the radiation on a temperature detector 70 and a synthetic detector 72. Detectors 70 and 72 may be of the lead sulfide type. Each filter 62 and 64 is designed to pass radiation in a select spectral band. Radiation not within the pass band of filters 62 and 64 is reflected by these filters to beam splitter 54 and does not reach temperature detector 70 or synthetic detector 72.

The portion of radiation 42 transmitted through the first beam splitter 54, that is, beam 58, impinges on a second beam splitter 74. The second beam splitter 74 splits beam 58 into three beams 76, 84 and 92. Band pass filters 78, 86 and 94 are positioned in the respective paths of beam 76, 84 and 92. Lenses 80, 88 and 96 focus the radiation on a cellulose detector 82, a measure detector 90 and a reference detector 98. Detectors 82, 90 and 98 also may be of the lead sulfide type. Each filter 78, 86 and 94 is selected so that it passes radiation in a separate band of the spectrum. Thus, a radiation 42 enters the upper head 24 through detector aperture 36, but the optics in the upper head 24 split the radiation 42 into five beams 56, 60, 76, 84 and 92 each of which is detected by an associated infrared detector 70, 72, 82, 90 and 98.

In a similar manner, the lower head 22 includes a light pipe 51 which guides radiation 42 to a collimating lens 53 between the light pipe 51 and a first beam splitter 55. The first beam splitter 55 splits radiation 42 into three separate beams 57, 59 and 61. Band pass filters 63 and 65 are positioned in the respective paths of beams 57 and 61. Lenses 67 and 69 focus the radiation on a temperature detector 71 and synthetic detector 73. Detectors 71 and 73 may be of the lead sulfide type. Each filter 63 and 65 is selected so that it passes radiation in a separate band of the spectrum. Radiation not within the pass band of filters 63 and 65 is reflected by these filters to the first beam splitter 55 and does not reach temperature detector 71 or synthetic detector 73.

The portion of radiation 42 transmitting through first beam splitter 55, that is, beam 59, impinges on a second beam splitter 75. The second beam splitter 75 splits the beam 59 into three separate beams 77, 85 and 93. Band pass filters 79, 87 and 95 are positioned in the respective paths of beam 77, 85 and 93. Lenses 81, 89 and 97 focus the radiation on a cellulose detector 83, a measure detector 91 and a reference detector 99. Detectors 83, 91 and 99 may be of the lead sulfide type. Each filter 79, 87 and 95 is selected so that it passes radiation in a separate band of the spectrum. Thus, radiation 42 enters the lower head 22 through detector aperture 37, but the optics in the lower head 22 split up the radiation 42 into five beams 57, 61, 77, 85 and 93, each of which is detected by an associated detector 71, 73, 83, 91 and 99.

Bandpass filters in the upper head 24 are made to be substantially similar to the filters in the lower head 22 with the same function. Thus, filter 62 is substantially similar to filter 63; filter 64 is similar to filter 65; filter 78 is similar to filter 79; filter 86 is similar to filter 87; and filter 94 is similar to filter 95.

Figure 9:
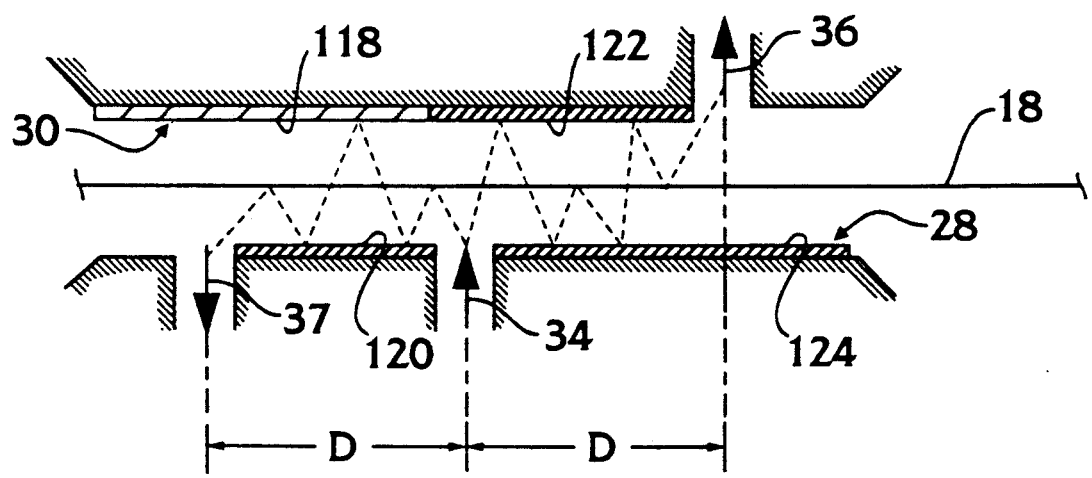
FIG. 9 illustrates an alternative embodiment for the source and detector apertures of the reflective paper guides and a possible variation for the surface of the paper guides.

FIG. 9 illustrates an alternative arrangement for source aperture 34 and detector apertures 36 and 37. The source aperture 34 and detector aperture 37 have the same locations as that shown in FIG. 2, but the detector aperture 36 would move to the right. Nonetheless, detector apertures 36 and 37 would still have substantially the same offset D from the source aperture 34. As shown in FIG. 9, the guides 28 and 30 would include a quartz layer 120, 122 and 124 with a reflective backing (not shown) and a radiation absorbing medium 118.

The advantage of this arrangement is it reduces the dependence on the transmitted portion of the radiation reaching detector aperture 37 and thereby enhances its dependence on scattering. The ultimate advantage would be in the reduction of number of grade groups required to calibrate the sensor 32.

Figure 4:
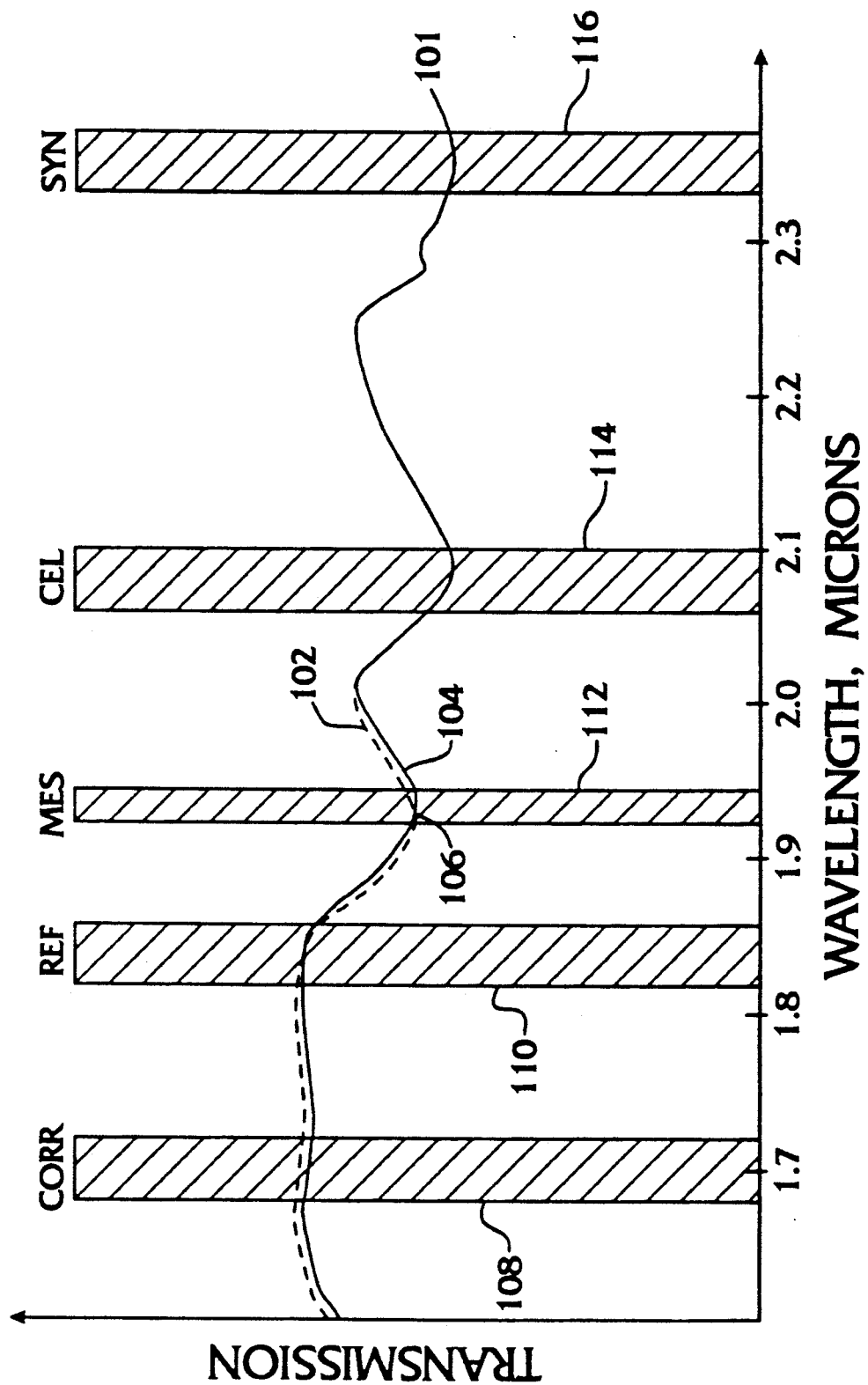
FIG. 4 illustrates the infrared transmission spectra of a light weight paper sheet, containing moisture, at two different temperatures with indication of appropriate detected measure, reference, temperature correction, cellulose and synthetic wavelength bands.

FIG. 4 illustrates the infrared transmission spectrum 101 of a light weight paper sheet, e.g., 70 grams/meter$^2$ (g/m$^2$), containing moisture, at a temperature of approximately 22° C. and of 60° C. The cross-hatched areas denoted MES, REF, CORR, CEL and SYN indicate the wavelength bands detected by measure detector 90, reference detector 98, temperature correction detector 70, cellulose detector 82 and synthetic detector 72 in upper head 24 (FIG. 2). Similarly, the cross-hatched areas MES, REF, CORR, CEL and SYN indicate the wavelength bands detected by measure detector 91, reference detector 99, temperature correction detector 71, cellulose detector 83 and synthetic detector 73 in the lower head 22.

To obtain the data for the infrared transmission spectrum 101, two plates of glass are placed on the opposing sides of a paper sheet and act to prevent loss of moisture during heating between the desired temperatures. The plates of glass serve not only to maintain constant moisture values during the measurements, but also to provide a thermal mass which maintains the paper sheet temperature to make possible measurements at temperatures above the ambient or at a lower temperature. To accomplish this, the glass-enclosed paper sheet is first heated, then measurements of the infrared transmission through the glass enclosing the paper sheet are made at the higher and lower temperatures.

The infrared absorption spectrum of water and paper is peculiar in that the absorption characteristics of the entire spectrum shift to shorter wavelengths as the paper sheet temperature is increased and to longer wavelengths as the paper sheet temperature decreases. As illustrated in FIG. 4, The infrared spectra of the light weight paper sheet at the higher temperature is shown by the dashed line 102. The infrared spectra at the lower temperature is shown by the solid line 104. Of course, the infrared spectrum 102 of the paper sheet at the higher temperature has approximately the same absorption characteristic as the lower temperature paper sheet, but at shorter wavelengths.

The infrared spectrum is affected by both the absorption by water and by paper fibers. In the band around 1.93 microns wavelength, water is much more efficient at absorbing infrared radiation than paper fibers. Thus, in this band of the spectrum the absorption is most strongly affected by the water content of the paper 18.

As shown in FIG. 4, for a light weight paper sheet (e.g., 70 g/m$^2$), an infrared band pass filter 86 (FIG. 2) associated with a measure detector 90 may have its pass band 112 approximately centered around the water absorption peak 106, for example, at approximately 1.93 microns. For this purpose, we may use a band pass filter 86 (FIG. 2) with a range from 1.92 to 1.95 microns, the lower and upper wavelengths at which the transmission reaches half that which is achieved at the transmission peak.

In this way, as the sheet temperature increases, the intensity of detected infrared radiation in the MES band increases at the long wavelength side of the band, while an approximately equal decrease in detected infrared radiation occurs at the opposite short wavelength side of the band. With this technique, the total amount of infrared radiation reaching the measure detector 90 is strongly sensitive to the moisture content and substantially insensitive to sheet temperature. Thus, the signal from measure detector 90 (the "MES" signal) provides a rough measurement of the sheet moisture content which is substantially insensitive to temperature change.

As mentioned earlier, the basis weight of the paper 18 also affects the infrared transmission spectrum. To provide a signal which is sensitive to the basis weight, as shown in FIG. 2, a band pass filter 94 is positioned before a reference detector 98. The filter 94 has its pass band 110 (FIG. 4) defining a REF band which is less sensitive to water and substantially insensitive to the sheet temperature. For example, a filter with a band pass range from 1.82 to 1.86 microns (normal incidence) has both of these characteristics. Because the pass band 110 of the filter is less than 1.9 microns, it is sensitive to the basis weight of paper 18. Accordingly, as the basis weight increases, the amount of infrared radiation passing through the sheet decreases. Thus, the signal from detector 98 (the "REF" signal) provides a rough measurement of the basis weight of the paper.

Because the MES and REF signals may be sensitive to the sheet temperature, the invention provides a temperature correction detector 70 (FIG. 2) for temperature correction with an associated band pass filter 62.

The signal from this temperature correction detector 70 (the "CORR" signal) may be used to correct the measurement of the sensor 32 for the effects of varying sheet temperature as described below. The pass band 108 chosen for this filter 62 passes radiation in a band of the transmission spectrum 101 so that the amplitude of the signal from the temperature correction detector 70 is sensitive to changes in the sheet temperature. The changes in the CORR signal from the temperature correction detector 70 are used to compensate for temperature induced changes in the MES and/or REF signals.

A preferred position for the detected CORR band or pass band 108 of this filter is shown in FIG. 4. For example, a band pass filter of 1.68 to 1.72 microns passes a band of the infrared spectrum where favorable temperature correction has been achieved for light weight paper.

The invention may also provide a cellulose detector 82 (FIG. 2) with an associated band pass filter 78. The signal from this cellulose detector 82 (the "CEL" signal) may be used to correct the moisture measurement for varying cellulose content or to provide a measurement of the moisture content as a percentage of the total sheet weight. The pass band 114 chosen for this filter 78 passes radiation in a band of the transmission spectrum 101 that is sensitive to the cellulose content of the paper 18.

A preferred position for the detected CEL band or pass band 114 of this filter is shown in FIG. 4. For example, a band pass filter of 2.06 to 2.10 microns passes a band of the infrared spectrum where favorable temperature correction has been achieved for light weight paper.

The invention may also provide a synthetic detector 72 (FIG. 2) with an associated band pass filter 64. The signal from this synthetic detector 72 (the "SYN" signal) may be used to correct the moisture measurement for varying synthetic content. Although relatively less common in paper products, synthetic fibers (e.g., polyester fibers and polyethylene fiber) may be included in light weight paper products (e.g., tea bags) to strengthen the paper to avoid bursting when wet. The pass band 116 chosen for this filter 72 passes radiation in a band of the transmission spectrum 101 that is sensitive to the synthetic fiber content of the paper 18.

A preferred position for the detected SYN band or pass band 108 of this filter is shown in FIG. 4. For example, a band pass filter of 2.33 to 2.37 microns passes a band of the infrared spectrum where favorable synthetic detection has been achieved for light weight paper.

It is preferred that an identical set of band pass filters be arranged in like manner in the lower head 22.

Figure 5:
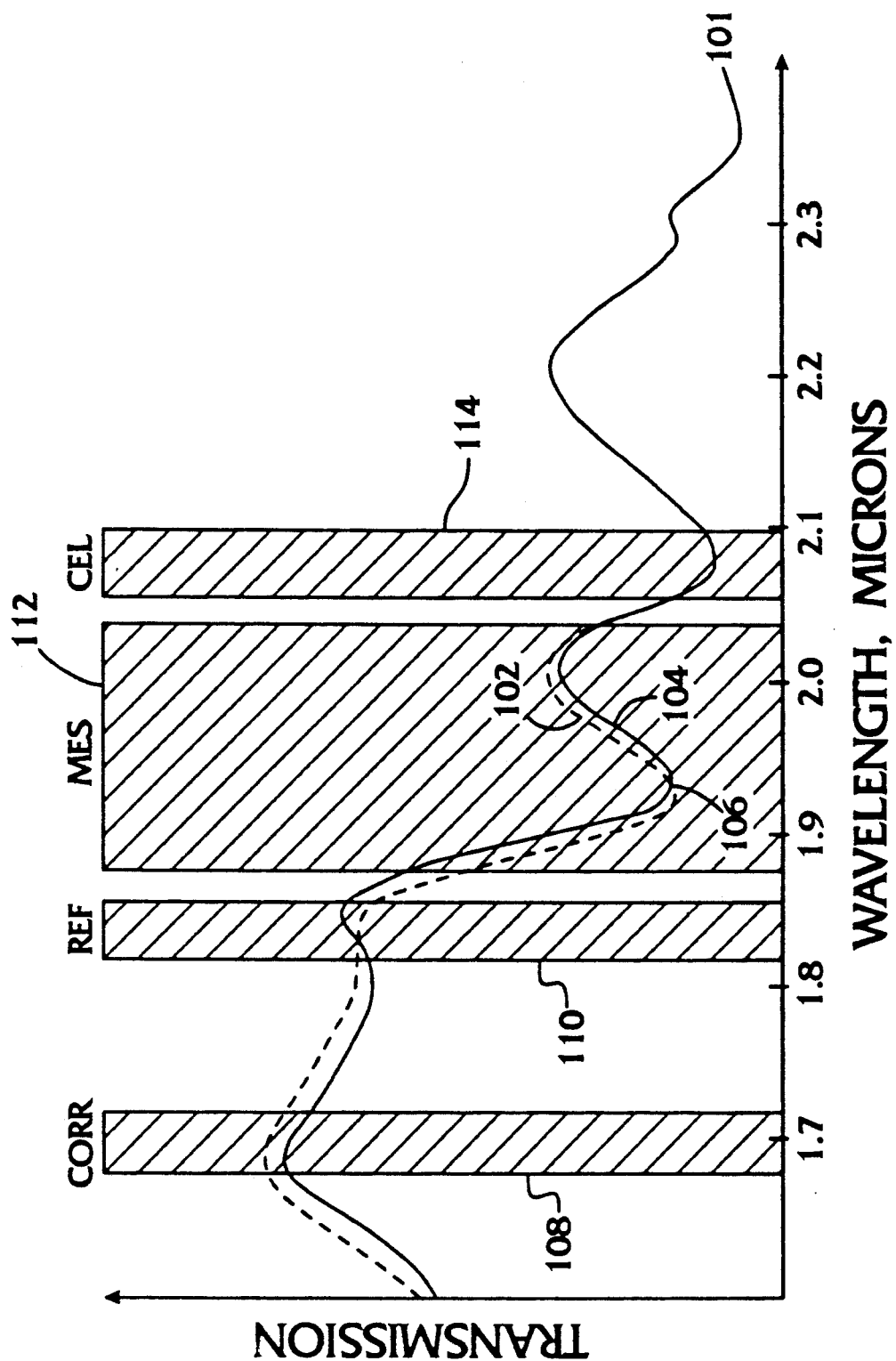
FIG. 5 illustrates the infrared transmission spectra of a medium weight paper sheet, containing moisture, at two different temperatures with indication of appropriate detected measure, reference, temperature correction and cellulose wavelength bands.

FIG. 5 illustrates the infrared transmission spectrum 101 for a medium weight paper sheet (e.g., a 205 g/m$^2$ liner board), containing moisture at a temperature of approximately 22° C. and of 60° C. The infrared spectrum of the sheet at the higher temperature is shown by the dashed line 102. The infrared spectrum of the sheet at the lower temperature is shown by the solid line 104. To obtain the infrared spectrum, the paper sheet was sealed between two plates of glass to prevent loss of moisture during heating. Then measurements of the infrared penetration through the glass enclosed sheets were made at the higher and lower temperature. The cross-hatched areas denoted MES, REF, CORR and CEL again illustrate the separate wavelength bands to be passed through the respective filters and detected.

As mentioned earlier, a heavier weight paper product typically contains more moisture than a light weight paper. As the amount of moisture increases, the water absorption peak increases in magnitude as well as broadens in the wavelength direction. As illustrated by FIG. 5, both of these effects tend to reduce the amount of radiation transmitted through the sheet. In fact, at and around the water absorption peak, the strong water and cellulose absorptions of a heavier grades of paper may effectively absorb much of the infrared radiation directed at the sheet from the infrared source. Thus, the narrow band pass filter as used for the light weight paper discussed earlier may be entirely inadequate in terms of passing the required amount of radiation to the detector.

Rather than selecting such a narrow band pass filter to pass infrared radiation in a band adjacent to the water absorption peak, the invention overcomes the problem of relatively low transmission by providing a relatively broad band pass filter around the water absorption peak. This also minimizes temperature sensitivity by ensuring that the integrated areas beneath the infrared transmission spectrum for a wide range of temperatures remain roughly equal and that the water absorption peak remains within the filter envelope.

For this medium weight paper sheet, an infrared band pass filter 86 (FIG. 2) associated with the measure detector 90 may have its pass band 112 around the water absorption peak 106. For this purpose, we may use a band pass filter 86 (FIG. 2) with a range from 1.88 to 2.04 microns (at normal incidence).

In this way, as the sheet temperature increases, the absorption peak remains within the pass band 112, and the intensity of detected infrared radiation in the MES band increases at the long wavelength side of the band, while an approximately equal decrease in detected infrared radiation occurs at the opposite short wavelength side of the band. With this technique, the total amount of infrared radiation reaching the measure detector 90 is strongly sensitive to the moisture content and substantially insensitive to sheet temperature. This is because total amount of infrared radiation reaching the measure detector 90 is proportional to the integrated area underneath the transmission curve. Thus, the signal from measure detector 90 (the "MES" signal) provides a rough measurement of the sheet moisture content which is substantially temperature insensitive.

As previously mentioned, the infrared absorption spectrum is also affected by the basis weight of the paper 18. To provide a signal dependent upon the basis weight of the paper 18, a band pass filter 94 is positioned before a reference detector 98. As shown by FIG. 5, this filter 94 has its pass band 110 at a wavelength band which is less sensitive to water and substantially insensitive to the sheet temperature. For example, a band pass filter with a range from 1.82 to 1.86 microns (normal incidence) has both of these characteristics. Because the pass band 110 of this filter 94 is less than 1.9 microns, it is also sensitive to the basis weight of the paper 18. Accordingly, as the basis weight increases, the amount of infrared radiation which passes through the paper 18 decreases. Thus, the signal from this reference detector 98 (the "REF" signal) provides a rough measurement of the basis weight of the paper.

As in the measurement of the light weight paper, because the MES and REF signals may still be sensitive to the sheet temperature, the invention provides a temperature correction detector 70 (FIG. 2) for temperature correction with an associated infrared band pass filter 62. The signal from this temperature correction detector 70 (the "CORR" signal) may be used to correct the moisture measurement of the sensor 32 for the effects of varying sheet temperature. The pass band 108 chosen for this filter 62 passes radiation in a band of the transmission spectrum 101 so that the amplitude of the signal from the temperature correction detector 70 is sensitive to changes in the sheet temperature. The changes in the CORR signal from the temperature correction detector are used to compensate for the temperature induced changes in the MES signal.

A preferred position for the detected CORR band or pass band 108 of this filter is shown in FIG. 5. For example, a band pass filter of 1.68 to 1.72 microns passes a band of the infrared spectrum where favorable temperature correction has been achieved for medium weight paper.

The invention may also provide a cellulose detector 82 (FIG. 2) with an associated band pass filter 78. The signal from this cellulose detector 82 (the "CEL" signal) may be used to correct the moisture measurement for varying cellulose content. The pass band 114 chosen for this filter 78 passes radiation in a band of the transmission spectrum 101 that is sensitive to the cellulose content of the paper 18.

A preferred position for the detected CEL band or pass band 114 of this filter is shown in FIG. 5. For example, a band pass filter of 2.06 to 2.10 microns passes a band of the infrared spectrum where favorable temperature correction has been achieved for medium weight paper.

Again it is preferred that an identical set of band pass filters be arranged in like manner in the lower head 22.

Figure 6:
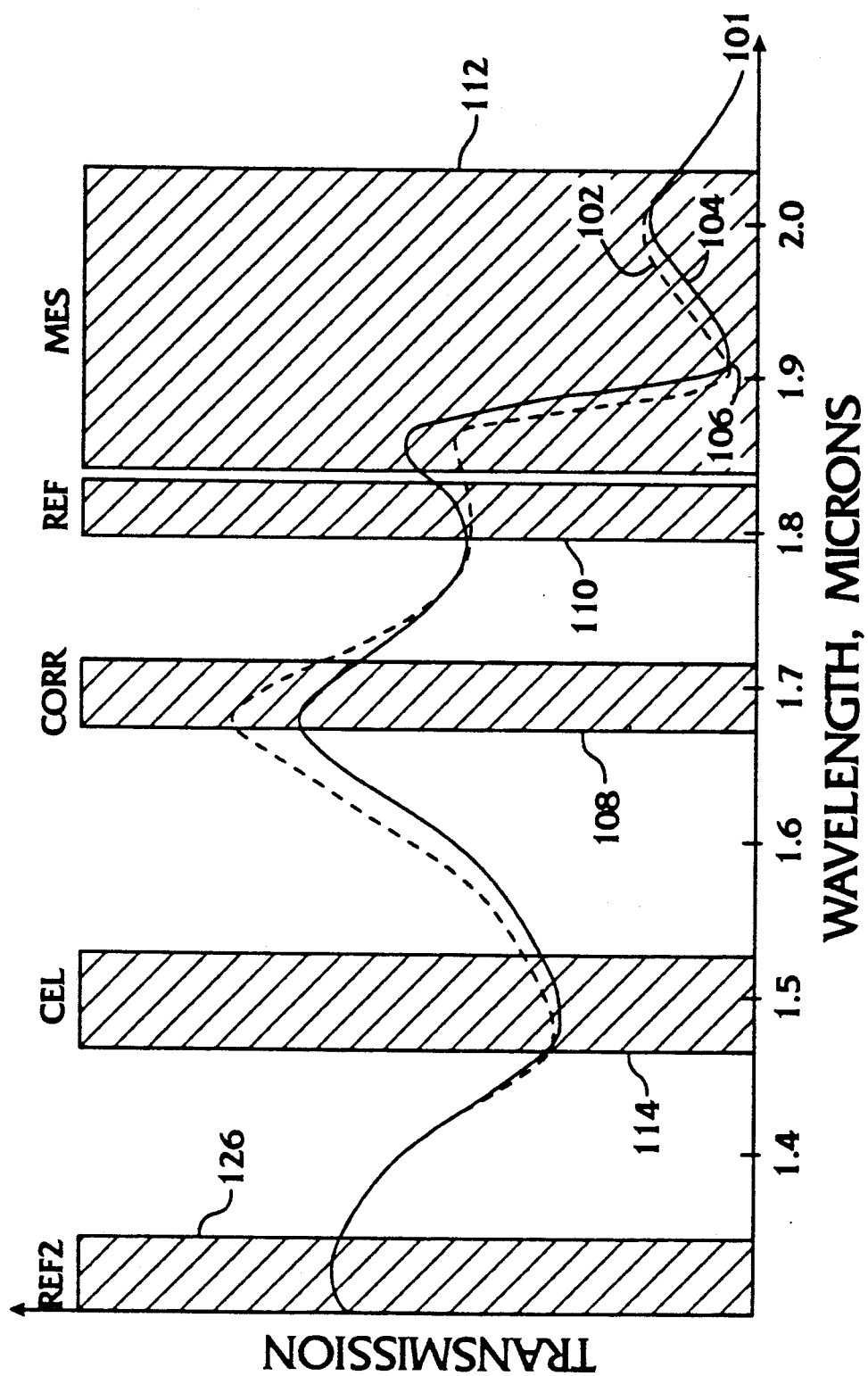
FIG. 6 illustrates the infrared transmission spectra of a heavy weight paper sheet, containing moisture, at two different temperatures with indication of appropriate detected measure, reference, temperature correction, cellulose and second reference wavelength bands.

FIG. 6 illustrates the infrared transmission spectrum 101 for a heavy weight paper sheet (e.g., a 345 g/m$^2$ liner board), containing moisture, at a temperature of approximately 22° C. and of 60° C. As in FIGS. 4-5, the infrared spectrum of the sheet at the higher temperature is shown by the dashed line 102. The infrared spectrum of the sheet at the lower temperature is again shown by the solid line 104. To obtain the infrared spectrum, the paper sheet was again sealed between two plates of glass to prevent loss of moisture during heating then measurements of the infrared penetration through the glass-enclosed sheets are made at the higher temperature and at the ambient or room temperature. The crosshatched areas designated MES, REF, CORR, CEL and REF2 illustrate the separate wavelength bands to be passed through the respective filters and detected.

As mentioned earlier, a heavier grade of paper typically contains more moisture than a lighter weight paper. As the amount of moisture increases even more than that contained in a medium weight paper sheet, the water absorption peak increases in magnitude as well as broadens in the wavelength direction even more. As illustrated by FIG. 6, both of these effects tend to further reduce the amount of radiation transmitted through the sheet. In fact, around the water absorption peak, the strong water and cellulose absorptions of the heavier grades of paper absorb much of the infrared radiation directed at the sheet from the infrared source. Thus, a narrow band pass filter as specified for the light weight paper, or even the broader band pass filter specified for the medium weight paper may be inadequate to pass the required amount of radiation to the detector.

The invention overcomes the problem of relatively low transmission by providing an even broader band pass filter around the water absorption peak than in the situations illustrated in FIGS. 4 and 5. This also reduces temperature sensitivity by ensuring the water absorption peak remains within the filter envelope.

For this heavy weight paper sheet, an infrared band pass filter 86 (FIG. 2) associated with the measure detector 90 may have its pass band 112 around the water absorption peak 106. For this purpose, we may use a band pass filter 86 (FIG. 2) with a range from 1.88 to 2.04 microns (at normal incidence).

In this way, as the sheet temperature increases the peak remains within the pass band, and the intensity of the infrared radiation increases on the long wavelength half of the filter 86, while a decrease in the intensity of the infrared radiation occurs at the opposite short wavelength half of the filter 86. However, this technique does not result in temperature insensitivity, because the total amount of infrared radiation reaching the measure detector 90 may not be substantially equal for the high and low temperatures. Thus, the measurement detector 90 is not only strongly dependent upon the moisture content of the paper 18, but may also be sensitive to the sheet temperature. Thus, the signal from measure detector 90 (the "MES" signal) provides a moisture measurement which may be temperature sensitive.

The infrared absorption spectrum is affected by the basis weight of the paper 18. To provide a signal sensitive to the basis weight of the paper 18, a band pass filter 94 is positioned before a reference detector 98. To compensate for any temperature sensitivity of the MES signal, the filter 94 has its pass band 110 defining a REF band which is less sensitive to the water in the sheet than the MES band surrounding the water absorption peak, but is sensitive to the sheet temperature. For example, a filter with a band pass range from 1.82 to 1.86 microns (normal incidence) has these characteristics. Because the pass band 110 of this filter 94 is less than 1.9 microns, it is also sensitive to the basis weight of the paper 18. Accordingly, as the basis weight increases, the amount of infrared radiation which passes through the paper 18 decreases. Thus, the signal from this detector 98 (the "REF" signal) provides a rough measurement of the basis weight of the paper.

Because the MES and REF signals may be sensitive to the sheet temperature, the invention provides a temperature correction detector 70 (FIG. 2) for temperature correction with an associated band pass filter 62. The signal from this temperature correction detector 70 (the "CORR" signal) may be used to correct the moisture measurement of the sensor 32 for the effects of varying sheet temperature. The pass band 108 chosen for this filter 62 passes radiation in a band of the transmission spectrum 101 so that the amplitude of the signal from the temperature correction detector 70 is sensitive to changes in the sheet temperature. The changes in the CORR signal from the temperature correction detector are used to compensate for the temperature induced changes in the MES signal.

A preferred position for the detected CORR band or pass band 108 of this filter is shown in FIG. 6. For example, a band pass filter of 1.68 to 1.72 microns passes a band of the infrared spectrum where favorable temperature correction has been achieved for medium weight paper.

The invention may also provide a cellulose detector 82 (FIG. 2) with an associated band pass filter 78. The signal from this cellulose detector 82 (the "CEL" signal) may be used to correct the moisture measurement for varying cellulose content. The pass band 114 chosen for this filter 78 passes radiation in a band of the transmission spectrum 101 that is sensitive to the cellulose content of the paper 18.

A preferred position for the detected CEL band or pass band 114 of this filter is shown in FIG. 6. For example, a band pass filter of 1.47 to 1.53 microns passes a band of the infrared spectrum where favorable temperature correction has been achieved for heavy weight paper.

Finally, the invention may also provide a second reference detector with an associated band pass filter. Although the second reference detector is not shown in FIG. 2, the second reference detector and associated filter could be disposed at the same physical location as the synthetic detector 72 and filter 78. The REF2 band or pass band 126 chosen for this filter passes radiation in a band of the transmission spectrum 101 that is less sensitive to the cellulose than the cellulose detector 82. Thus, the cellulose reference detector serves as a reference.

A preferred position for the REF2 band or pass band 126 of this filter is shown in FIG. 6. For example, a band pass filter of 1.30 to 1.34 microns passes a band of the infrared spectrum where favorable results have been achieved for heavy weight paper.

It is preferred that an identical set of band pass filters be arranged in like manner in the lower head 22.

Table 1 gives the appropriate band pass filters for basis weights of up to 550 g/m². Band pass ranges are expressed as the lower and upper wavelengths at which the transmission reaches half that which is achieved at the transmission peak.

TABLE 1

| Maximum Basis Weight g/m² | MES Filter microns | | REF Filter microns | | CORR Filter microns | | CEL Filter microns | | SYN/REF2 Filter microns | |
|---|---|---|---|---|---|---|---|---|---|---|
| | lower | upper | lower | upper | lower | upper | lower | upper | lower | upper |
| 70  | 1.92 | 1.95 | 1.82 | 1.86 | 1.68 | 1.72 | 2.06 | 2.10 | 2.33 | 2.37 |
| 150 | 1.90 | 2.01 | 1.78 | 1.82 | 1.68 | 1.72 | 2.06 | 2.10 | —    | —    |
| 250 | 1.88 | 2.04 | 1.82 | 1.86 | 1.68 | 1.72 | 2.06 | 2.10 | —    | —    |
| 325 | 1.87 | 2.05 | 1.82 | 1.86 | 1.68 | 1.72 | 1.47 | 1.53 | 1.30 | 1.34 |
| 550 | 1.84 | 2.03 | 1.82 | 1.86 | 1.68 | 1.72 | 1.47 | 1.53 | 1.30 | 1.34 |

The "Maximum Basis Weight" column specifies the maximum basis weight in g/m² of the paper product for which the filter set should be used. The maximum water weight is approximately no more than 10% for each grade of paper product. Thus, for a particular context, the customer specifies the maximum basis weight and the maximum percent moisture for the paper being manufactured and the appropriate filter sets are then selected from Table 1 which satisfy both of these conditions.

As shown in FIG. 2, the infrared radiation from lamp 38 is modulated by the tines 44 of the vibrating tuning fork 46. For the sake of simplicity the modulating of the radiation 42 is explained for the upper head 24 alone. However, the same arrangement is also preferred for the lower head 22. The output of each detector 70, 72, 82, 90 and 98 is sinusoidally modulated at the same frequency and phase as the detected infrared beams 56, 60, 76, 84 and 92. However, infrared energy from the paper 18 itself and from other external sources (not shown) will also reach the detectors. Thus, each detector signal also includes a DC component.

The output of each of the five detectors 70, 72, 82, 90 and 98 is transmitted to the signal processing circuitry 45. The circuitry 45 is designed to filter out the DC component of the detector signals. The filtered detector signals are then passed on to a phase synchronous demodulation circuit included within the signal processing circuitry 45. The purpose of the phase synchronous demodulator is to filter out changes in the signals from the detectors 70, 72, 82, 90 and 98 which are not caused by the varying infrared absorption of the paper 18. For example, 60 Hz line noise in the detector signals is filtered out by the demodulator circuit, as explained below.

A sine wave oscillator 43 drives the tines 44 of tuning fork 46 at its resonant frequency. The output of this oscillator 43 is converted to a square wave with the same frequency and phase as the sine waves driving the tuning fork 46. This square wave output 41 is fed to a phase synchronous demodulator portion of the signal processing circuitry 45, along with the filtered signals from each of the five detectors 70, 72, 82, 90 and 98. Of course, the filtered signals are modulated at the same frequency and phase as the output of oscillator 43. By demodulating the outputs from each of the detectors 70, 72, 82, 90 and 98 with a square wave having the same frequency and phase as the output of the oscillator 43 and averaging the demodulated outputs over a number of cycles, the sensor 32 filters out detector signals changes from changes in the intensity of external infrared sources or extraneous signals such as the 60 Hz line voltage. This filtering technique using a phase synchronized demodulation circuit is known. This reduces erroneous moisture measurements. The output signal of each detector indicates the intensity of radiation 42 passing through the associated band pass filter.

Figure 8:
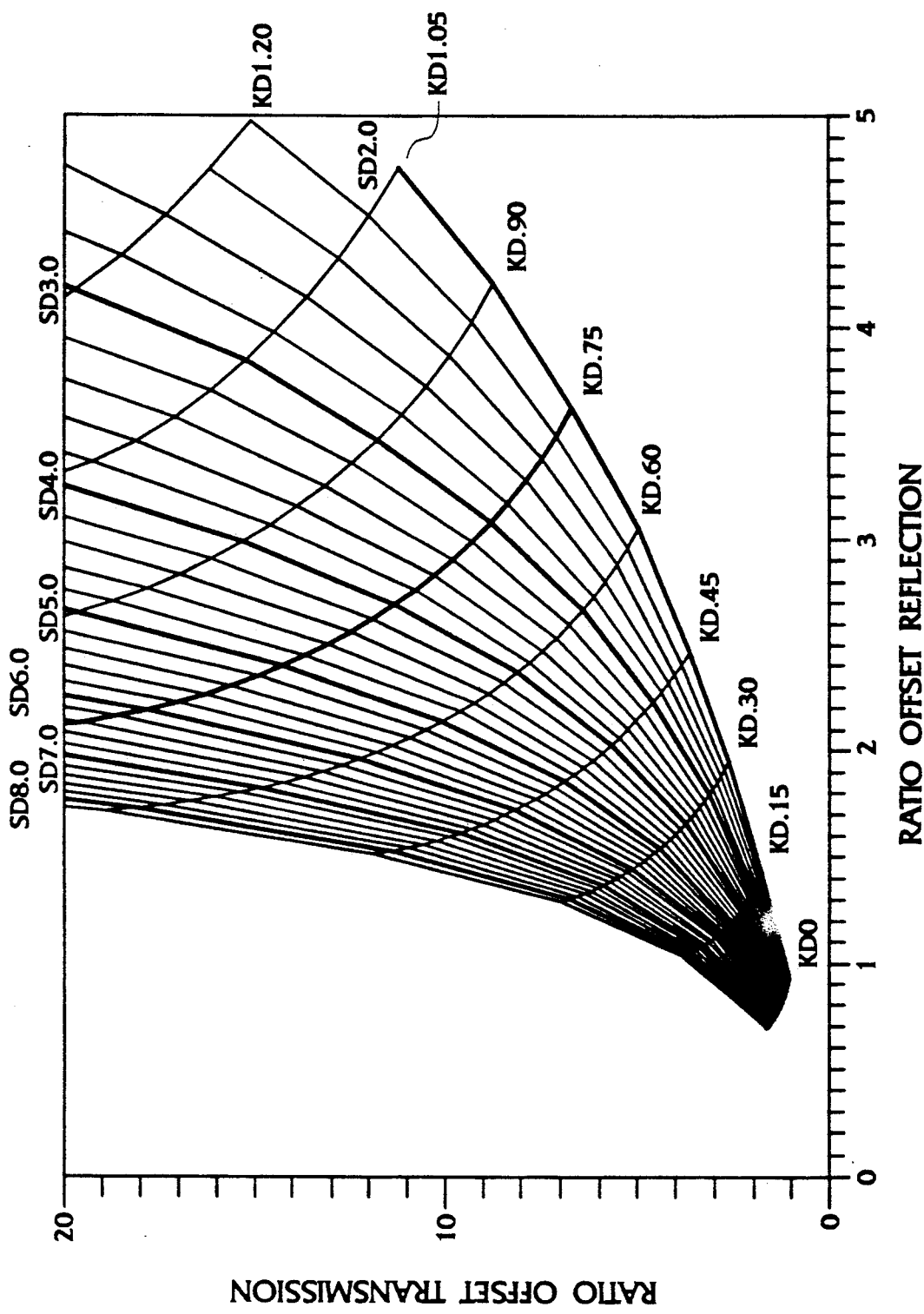
FIG. 8 illustrates a graph of the absorption and scattering powers of a paper sheet plotted as a function of the reciprocal of the intensity of radiation individually detected at a transmission and a reflection detector which are offset to the same degree from an infrared radiation source.

The invention provides a graph as shown in FIG. 8 from a mathematical analysis for determining the scattering and absorption power of diffuse media such as paper. The scattering and absorption powers are determined to be a function of the intensity of the detected radiation at both the lower and upper heads of the moisture sensor. The following analysis depends in part on the Kubelka-Munk theory. This theory describes the behavior of light interacting with diffuse media such as paper and provides a mathematical analysis for determining the amount of light transmitted through and reflected from the paper. W. Wendlandt and H. Hecht, *Reflectance Spectroscopy*, Chapter III (1966) provides a description of the Kubelka-Munk theory and is incorporated herein by reference.

Figure 7:
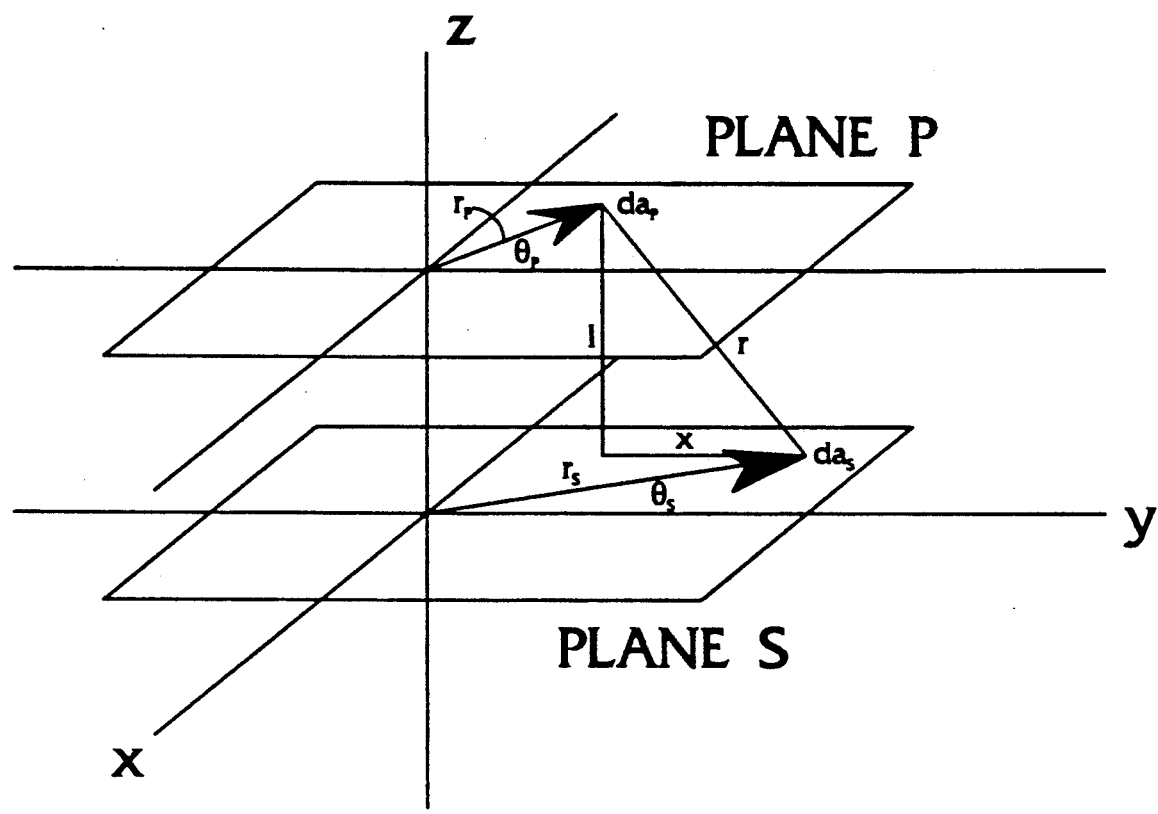
FIG. 7 illustrates the geometry and nomenclature used for the analysis of the light distribution on two parallel planes.

As shown in FIG. 7, the technique is best illustrated by an example which involves two parallel planes, S and P. It will be assumed that the planes act as Lambertian surfaces, that is, they are perfect diffusers of radiation and follow Lambert's law:

$$I(\Phi) = I_o \cos(\Phi)$$

where:

$\Phi$ = the angle from the normal to the surface and the direction of light leaving the surface $I(\Phi)$ = the intensity of light per unit solid angle leaving the surface in the direction $\Phi$ $I_o$ = the intensity of light per unit solid angle leaving the surface in the normal direction.

It also will be assumed that a radiation source is in plane S and is distributed symmetrically about an axis normal to the surfaces of planes and centered in the middle of the illuminated area of plane. Finally, it will be assumed that the sheet being measured acts as a diffusing material such as paper and has the reflection and transmission properties described by the theory of Kubelka and Munk.

The first step in the analysis is to determine the distribution of light incident on the surface of the parallel sheet facing the source from light coming from the source plane. The process used is that for every point on the parallel sheet, the total intensity of light reaching it from every point on the source plane is calculated.

FIG. 7 shows the two parallel planes, S and P. Consider an element of area $da_s$ at a point on the S plane located at radial distance $r_s$ and at angle $\Theta_s$ from the Y axis. The intensity of light per unit area per unit solid angle leaving normal to that surface at that point is given to be $i_s(r_s)$ (watts/cm$^2$*sr). The total light intensity reaching an element of area $da_p$ on plane P at $r_p$ and $\Theta_p$ from $da_s$ is given by:

$$d^2F(r_p, r_s, \Theta_s, \Theta_p, \Phi) = i_s(r_s) \cos(\Phi) \, da_s \, (da_p \cos(\Phi)/r^2)$$
(watts)

where r is the distance between $da_s$ and $da_p$. The first $\cos(\Phi)$ term on the right is from applying Lambert's law. The term in parentheses on the right is the solid angle subtended by $da_p$. The angle $\Phi$ is between the normal to the planes and a line drawn between $da_s$ and $da_p$. The intensity per unit area incident on $da_p$ from $da_s$ is:

$$df(r_p, r_s, \Theta_s, \Theta_p, \Phi) = i_s(r_s) \, da_s (\cos^2(\Phi)/r^2) \text{ (watts/cm}^2\text{)}$$

The value of $\cos(\Phi)$ can be written in terms of the separation between planes (l) and r:

$$\cos(\Phi) = l/r$$

The intensity per unit area becomes:

$$df(r_p, r_s, \Theta_s, \Theta_p, \Phi) = i_s(r_s) \, da_s (l^2/r^4) \text{ (watts/cm}^2\text{)}$$

The value of r can be written in terms of the position variables $r_p$, $r_s$, $\Theta_s$ and $\Theta_p$:

$$r = \text{sqrt}(l^2 + r_s^2 + r_p^2 - 2r_s r_p \cos(\Theta_s - \Theta_p))$$

The incremental area $da_s$ can also be written in terms of the position variables $r_s$ and $\Theta_s$.

$$da_s = r_s \, dr_s \, d\Theta_s$$

Combining we have the intensity per unit area in terms of position variables only:

$$df(r_p, r_s, \Theta_s, \Theta_p, \Phi) = i_s(r_s) \, r_s \, l^2 \, dr_s \, d\Theta_s /$$

$$(l^2 + r_s^2 + r_p^2 - 2r_s r_p \cos(\Theta_s - \Theta_p))^4 \text{ (watts/cm}^2\text{)}$$

To obtain the total intensity per unit area on elemental area $da_p$ on plane P from the entire surface of plane S, the equation above must be integrated over the entire surface from $r_s=0$ to $r_s=r_{smax}$, the maximum radius of plane S and $\Theta_s=0$ to $2\pi$:

$$d(r_p, \Theta_p) = \int_{r_s=0}^{r_{smax}} \int_{\Theta_s=0}^{2\pi} i_s(r_s) \, r_s \, l^2 /$$

$$(l^2 + r_s^2 + r_p^2 - 2r_s r_p \cos(\Theta_s - \Theta_p))^4 \, dr_s \, d\Theta_s \text{ (watts/cm}^2\text{)}$$

This integral is best solved by a numerical method. One suitable method is the trapezoidal method. To obtain the distribution of incident intensity on plane P, the integral must be solved at all positions of $r_p$ and $\Theta_p$.

If plane P represents a sheet of diffusing material between two planes, S and T (not shown), the distribution of incident light on plane P can be used to calculate the intensity of the reflected and transmitted light. If the sheet is paper, the theory of Kubelka-Munk provides an accurate way to calculate the reflected and transmitted light when the absorption and scattering coefficients are known. The transmission calculated from Kubelka-Munk theory multiplied by the incident light distribution on plane P is now a source distribution to plane T. Similarly, the reflection calculated from Kubelka-Munk theory multiplied by the incident light distribution on plane P is now a source distribution back to the plane S.

The same method is used again to determine the distribution of incident light on plane T. The incident light distribution on plane T is reflected back, becoming a source distribution of light which impinges on the back side of plane P. This light is reflected and transmitted by plane P as described above. The light thus transmitted adds to the light that was incident from plane S and is reflected back from plane P. This forms a new distribution of light that is now incident on the plane S.

The new distribution of light on plane S is the incident light from plane P reflected back plus the original illuminated area. With this new source distribution the calculations are repeated to find new distributions on all planes. After several iterations there will be no change, that is the results will have converged to a final value and additional iterations of the calculations will not produce different results.

Once the light distribution is known for planes S and T, the calculated light intensity can be determined for a detector placed anywhere on plane S or on plane T. Two positions have been analyzed in detail, but the same approach would work for any position. The positions analyzed are where: (1) the detector is on plane T and offset from the illuminated area; and (2) the detector is on plane S and offset the same distance from the source of light or the illuminated area. The former is referred to as a transmission detector and the latter as a reflection detector.

Up to this point we have shown that if the absorption and scattering coefficients of the sheet are known the intensity distribution of light on all planes can be calculated. In actual operation, a sensor would be set up to measure the intensity at two or more detector locations and then absorption and scattering coefficient would be determined. To implement this technique, the intensity distributions are calculated for all values of absorption and scattering coefficients likely to be encountered.

FIG. 8 illustrates a graph of the absorption and scattering powers of a paper sheet plotted as a function of the intensity of radiation individually detected at a transmission and a reflection detector which are offset to the same degree from an infrared radiation source. The ordinate of the graph is determined by calculating an intensity ratio from the transmission detector located on plane T. The abscissa is determined by calculating an intensity ratio from the reflection detector located on plane S. The intensity ratio for both detectors is defined as the intensity with no sheet of material between plane S and T to the intensity when the sheet of material is interposed therebetween. Contour lines connect equal absorption powers and equal scattering powers associated with those ratios.

To use a graph as illustrated in FIG. 8 the sheet to be measured is placed between the planes S and T. The intensity of a select signal, such as the MES signal, is measured by the detectors at the two locations. Next, the intensity is determined when there is no sheet interposed between planes S and T. The intensity ratio, that is, the intensity with no sheet in interposed divided by intensity with the sheet interposed is then calculated. The intensity ratios are then used to find the absorption and scattering powers of the sheet. Of course, by interpolating between the contour lines of equal absorption powers and equal scattering powers the actual value of absorption and scattering coefficients can be determined.

Two approaches can be used to correct temperature error in the absorption measurements. Under the first approach, we can assume that the temperature dependent part of the absorption coefficient can be separated:

$$k_i(T) = k_{io} f_i(T) \quad (1)$$

where $T$ = temperature;
$f_i(T)$ is a function that depends on temperature alone;
and $k_{io}$ = absorption coefficient of signal i at the calibration temperature.

We can also assume that the temperature function for any signal is a linear function of the temperature function of the correction signal:

$$f_i(T) = \alpha f_{corr}(T) + \beta \quad (2)$$

By combining (1) and (2) we have:

$$f_i(T) = \frac{\alpha_i}{k_{corr\Theta}} k_{corr}(T) + \beta$$

Then for each signal the corrected absorption coefficient is:

$$k_{io} = \frac{k_i(T)}{\frac{\alpha_i}{k_{corr\Theta}} k_{corr}(T) + \beta_i}$$

and $\alpha_i$ and $\beta_i$ would be determined experimentally.

A second approach to removing temperature error is to correct the ratios before determining the absorption coefficients. For each wavelength we have signal taken with no sheet at Standardize, REFS, and a signal on-sheet, REF. We then calculate a ratio for that wavelength:

RREF = REFS/REF,
    RMES = MESS/MES,
    RCEL = CELS/CEL, and

-continued
$$RCORR = CORRS/CORR.$$

Calculate a Temperature Correction Ratio:

$$RT = \frac{RCORR}{RREF} - \left(C1 + C2 \cdot \frac{RMES}{RREF} + C3 \cdot \frac{RCEL}{RREF}\right)$$

Coefficients C1, C2 and C3 are chosen so that RT is approximately zero at calibration temperature. Use this value to correct the signal for each wavelength:

$$RREFcor = RREF \cdot (1 + C4 \cdot RT),$$
$$RMEScor = RMES \cdot (1 + C5 \cdot RT), \text{ and}$$
$$RCELcor = RCEL \cdot (1 + C6 \cdot RT).$$

Once the absorption coefficients are known for the moisture and reference wavelengths the moisture calculation is straight forward. For the simple case of plain paper with no fillers or broad band absorbers:

$$k = k_{water} \cdot \%MOI/100 + k_{fiber} \cdot (1 - \%MOI/100)$$

where
$k$ = absorption coefficient of paper at 1.94 microns determined by the process described above
$k_{water}$ = absorption coefficient of water (a known constant)
$k_{fiber}$ = absorption coefficient of fiber (a known constant)
%MOI = percent moisture in paper
solving for %MOI $$\%MOI = (k - k_{fiber}) \cdot 100/(k_{water} - k_{fiber}) = ak + b$$

where a is a constant equal to $100/(k_{water} - k_{fiber})$ and is in a constant equal to $k_{fiber} \cdot a$ Thus, in principle a single wavelength is sufficient to determine moisture in the simplest case.

In the more realistic case where broad band absorbers are present then two wavelengths are required:

$$kmes = kmes_{water} \cdot \% MOI/100 + kmes_{fiber} \cdot (1 - \% MOI/100) + kmes_{bb} \cdot bbwt$$

and $$kref = kref_{water} \cdot \% MOI/100 + kref_{fiber} \cdot (1 - \% MOI/100) + kref_{bb} \cdot bbwt$$

where
kmes = absorption coefficient of paper at 1.94 micron
$kmes_{water}$ = absorption coefficient of water at 1.94 micron
$kmes_{fiber}$ = absorption coefficient of fiber at 1.94 micron
$kmes_{bb}$ = absorption coefficient of broad band absorber at 1.94 micron
kref = absorption coefficient of paper at 1.8 micron
$kref_{water}$ = absorption coefficient of water at 1.8 micron
$kref_{fiber}$ = absorption coefficient of fiber at 1.8 micron
$kref_{bb}$ = absorption coefficient of broad band absorber at 1.8 micron
bbwt = broad band absorber basis weight Since the absorption coefficients of the broad band absorber at the mes and ref wavelengths are the same, the difference between kmes and kref give the moisture without the effect of broadband absorption:

$$\% MOI = (dk - dk_{fiber}) \cdot 100/(dk_{water} - dk_{fiber})$$
$$= adk + b$$

where
dk = kmes − kref;
$a = 100/(dk_{water} - dk_{fiber})$; and
$b = -dk_{fiber} \cdot a$ Sometimes a better approximation is obtained by using a polynomial of dk where $$\%MOI = adk + b(dk)^2 + C$$

Based on these measurements, a sheet moisture correction can be accomplished manually. However, many modern paper mills are highly automated. In these paper mills, the signals produced by the sensor 32 are preferably fed to a computer 47 which computes the sheet moisture profile using the signals from the detectors and then, based on this computation, selectively activates one or more known devices 49 for altering the moisture content of certain portions of the paper 18. Many such devices 49 for altering the sheet moisture profile exist, including such devices as selectively controllable water showers for increasing the moisture content of select cross-directional sections of paper 18 and/or infrared heaters for selectively drying such sections of paper 18.

We claim:

1. A sensor for measuring one or more select components of a sheet, comprising:
a radiation source for emitting radiation toward the sheet;
a plurality of detecting means for detecting radiation after interaction with the sheet; and
means for directing the radiation so that the radiation makes multiple interactions with the sheet in moving from the source to the detecting means, wherein the directing means includes a first reflector and a second reflector defining a sheet space for the sheet to occupy, wherein the first reflector includes a source aperture for emitting radiation and a first detector aperture, offset from the source aperture, for directing radiation to at least one detecting means and wherein the second reflector includes a second detector aperture, offset substantially the same distance as the first detector aperture from the source aperture, for directing radiation to at least one detecting means.

2. The sensor of claim 1, wherein the first and second reflectors include diffuse surfaces facing and substantially parallel to the sheet.

3. The sensor of claim 1, further comprising means for computing a ratio of the intensity of the detected radiation when the sheet is absent from the sheet space and the intensity of the detected radiation when the sheet occupies the sheet space.

4. The sensor of claim 3, further comprising means for computing a first ratio based on the radiation received at the first detector aperture and a second ratio based on the radiation received at the second detector aperture.

5. The sensor of claim 4, further comprising means for computing an absorption and scattering power of the sheet from the first and second intensity ratios.

6. The sensor of claim 5, wherein the detecting means includes a first detector for detecting and generating a first signal indicative of the intensity of the radiation in a first band of the spectrum which is sensitive to a first component of the sheet.

7. The sensor of claim 6, wherein the detecting means includes a second detector for detecting and generating a second signal indicative of the intensity of the radiation in a second band of the spectrum which is less sensitive to the first component than the first band.

8. The sensor of claim 7, wherein the detecting means includes a third detector for detecting and generating a third signal indicative of the intensity of the radiation in a third band of the spectrum which is sensitive to temperature.

9. The sensor of claim 8, further comprising means for computing a first, second and third absorption powers, of the sheet based on the first, second and third signals.

10. The sensor of claim 9, further comprising means for correcting the first and the second absorption powers for the temperature of the sheet based on the third absorption power.

11. The sensor of claim 9, wherein the detecting means includes a fourth detector for detecting and generating a fourth signal indicative of the intensity of the radiation at a fourth band of the spectrum which is sensitive to a second component of the sheet.

12. The sensor of claim 11, wherein the detecting means includes a fifth detector for detecting and generating a fifth signal indicative of the intensity of the radiation at a fifth band of the spectrum which is sensitive to a third component in the sheet.

13. The sensor of claim 12, further comprising means for computing a fourth absorption power of the sheet from the fourth signal.

14. The sensor of claim 13, further comprising means for computing a fifth absorption power of the sheet from the fifth signal.

15. The sensor of claim 14, further comprising means for correcting the fourth and fifth absorption powers for the sheet temperature based on the third absorption power.

16. The sensor of claim 12, wherein the sheet is paper, the first component is moisture, the second component is cellulose, the third component is synthetic fiber and the radiation is in the infrared spectrum.

17. A sensor for measuring one or more select components of a sheet, comprising:
a source for emitting radiation through a source aperture;
means for detecting radiation after the radiation has multiple interactions with the sheet, including at least two detector apertures, with substantially the same offset from the source aperture, for receiving the radiation; and
first and second reflector means for directing the radiation so that the radiation has multiple interactions with the sheet when moving from the source to the detecting means.

18. A method for measuring the amount of a select component of a sheet comprising the steps of:
emitting radiation from a source to the sheet;
detecting and generating a plurality of signals indicative of the intensity of the radiation emerging from the sheet at a plurality of detecting means with substantially equal offset from the radiation source; and
directing the radiation so that the radiation makes multiple interactions with the sheet in moving from the source to the detecting means.

19. The method of claim 18, further comprising the step of:
calculating, with a computer, the amount of the select component using the plurality of signals.

20. A sensor for measuring one or more select components of a sheet, comprising:
a radiation source for emitting radiation toward the sheet;
a plurality of detecting means, offset substantially the same from the source, for detecting radiation after interaction with the sheet, wherein the detecting means includes a first detector for detecting and generating a first signal indicative of the intensity of the radiation in a first band of the spectrum which is sensitive to a first component of the sheet, a second detector for detecting and generating a second signal indicative of the intensity of the radiation in a second band of the spectrum which is less sensitive to the first component than the first band, a third detector for detecting and generating a third signal indicative of the intensity of the radiation in a third band of the spectrum which is sensitive to temperature, and a fourth detector for detecting and generating a fourth signal indicative of the intensity of the radiation at a fourth band of the spectrum which is sensitive to a second component of the sheet;
means for directing the radiation so that the radiation makes multiple interactions with the sheet in moving from the source to the detecting means, wherein the directing means includes a first reflector and second reflector defining a sheet space for the sheet to occupy;
means for computing a ratio of the intensity of the detected radiation when the sheet is absent from the sheet space and the intensity of the detected radiation when the sheet occupies the sheet space;
means for computing a first intensity ratio based on the radiation received at a first detector aperture and a second intensity ratio based on the radiation received at a second detector aperture; and
means for computing an absorption and scattering power of the sheet from the first and second intensity ratios.

21. The sensor of claim 20, wherein the detecting means includes a fifth detector for detecting and generating a fifth signal indicative of the intensity of the radiation at a fifth band of the spectrum which is sensitive to a third component in the sheet.

22. The sensor of claim 21, further comprising means for computing a fifth absorption power of the sheet from the fifth signal.

23. The sensor of claim 21, wherein the sheet is paper, the first component is moisture, the second component is cellulose, the third component is synthetic fiber and the radiation is in the infrared spectrum.

24. The sensor of claim 20, further comprising means for computing a fourth absorption power of the sheet from the fourth signal.

25. A sensor for measuring one or more select components of a sheet, comprising:
a radiation source for emitting radiation toward the sheet;
a plurality of detecting means, offset substantially the same from the source, for detecting radiation after interaction with the sheet, wherein the detecting means includes a first detector for detecting and generating a first signal indicative of the intensity of the radiation in a first band of the spectrum which is sensitive to a first component of the sheet, a second detector for detecting and generating a second signal indicative of the intensity of the radiation in a second band of the spectrum which is less sensitive to the first component than the first band, a third detector for detecting and generating a third signal indicative of the intensity of the radiation in a third band of the spectrum which is sensitive to temperature, a fourth detector for detecting and generating a fourth signal indicative of the intensity of the radiation at a fourth band of the spectrum which is sensitive to a second component of the sheet, and a fifth detector for detecting and generating a fifth signal indicative of the intensity of the radiation at a fifth band of the spectrum which is sensitive to a third component in the sheet;

means for directing the radiation so that the radiation makes multiple interactions with the sheet in moving from the source to the detecting means, wherein the directing means includes a first reflector and second reflector defining a sheet space for the sheet to occupy;

means for computing a ratio of the intensity of the detected radiation when the sheet is absent from the sheet space and the intensity of the detected radiation when the sheet occupies the sheet space;

means for computing a first ratio based on the radiation received at a first detector aperture and a second intensity ratio based on the radiation received at a second detector aperture;

means for computing an absorption and scattering power of the sheet from the first and second intensity ratios;

means for computing first, second, third, fourth and fifth absorption powers based on the first, second third, fourth and fifth signals; and means for correcting the first, second, fourth and fifth absorption powers for the sheet temperature based on the third absorption power.

* * * * *

UNITED STATES PATENT AND TRADEMARK OFFICE
CERTIFICATE OF CORRECTION

PATENT NO. : 5,276,327

DATED : January 4, 1994

INVENTOR(S) : David A. Bossen et al.

It is certified that error appears in the above-identified patent and that said Letters Patent is hereby corrected as shown below:

On title page, in the "[*] Notice:"

section), after "subsequent to: and before "has been", change "May 4, 2010" to --August 10, 2010--.

Signed and Sealed this

Fourteenth Day of June, 1994

*Attest:*

BRUCE LEHMAN

*Attesting Officer*     *Commissioner of Patents and Trademarks*